United States Patent [19]

Horiguchi et al.

[11] 4,406,160

[45] Sep. 27, 1983

[54] METHOD OF INSPECTING A RESIST LAYER ON A GRAVURE PRINTING PLATE, AND DEVICE FOR PRACTICING SAME

[75] Inventors: Satoru Horiguchi, Saitama; Shinichi Amemiya, Tokyo, both of Japan

[73] Assignee: Dai Nippon Insatsu Kabushiki Kaisha, Tokyo, Japan

[21] Appl. No.: 173,816

[22] Filed: Jul. 30, 1980

[30] Foreign Application Priority Data

Aug. 2, 1979 [JP] Japan .................................. 54-98845
Jan. 24, 1980 [JP] Japan .................................. 55-6343

[51] Int. Cl.[3] ...................... G01N 33/22; G01N 33/44
[52] U.S. Cl. ...................................... 73/73; 73/150 R
[58] Field of Search .............................. 73/73, 150, 38

[56] References Cited

U.S. PATENT DOCUMENTS 2,491,687 12/1949 Pollock .................................. 73/73
3,028,755 4/1962 Carter .................................... 73/73

*Primary Examiner*—S. Clement Swisher
*Attorney, Agent, or Firm*—Parkhurst & Oliff

[57] ABSTRACT

An inspecting liquid is dropped onto a resist layer formed on a gravure printing plate and is allowed to permeate the resist layer to reach the printing plate so that a short circuit is formed between the inspecting liquid and the printing plate. The time required for forming the short circuit is measured to determine the conditions of the resist layer thereby to improve the quality of the finished printing plate.

3 Claims, 16 Drawing Figures

FIG. 2
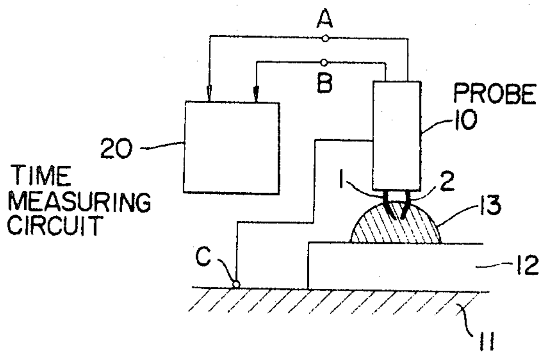
FIG. 1
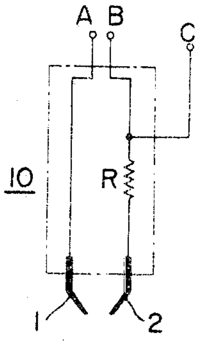
FIG. 3
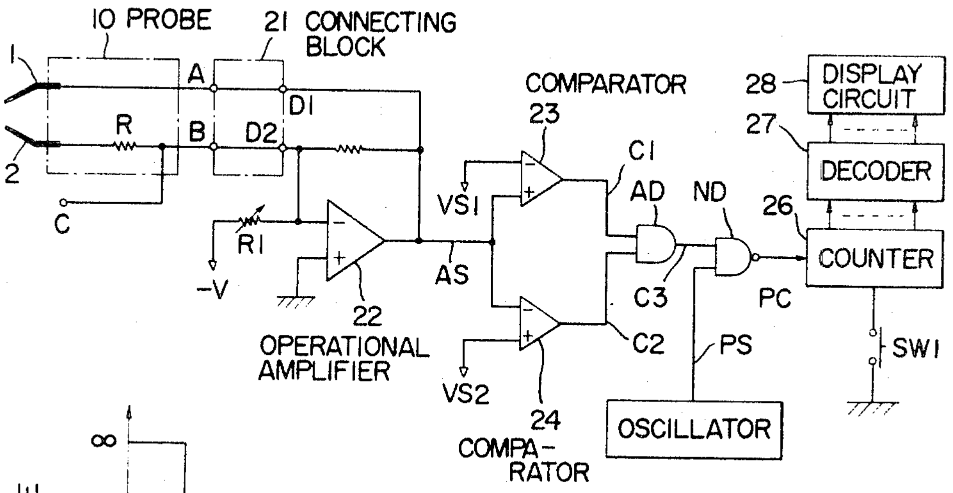
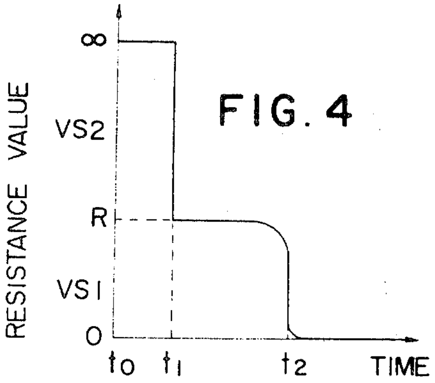
FIG. 4
FIG. 5
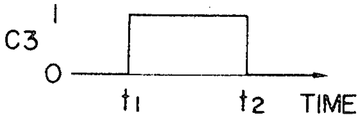

(A)

(B)

METHOD OF INSPECTING A RESIST LAYER ON A GRAVURE PRINTING PLATE, AND DEVICE FOR PRACTICING SAME

BACKGROUND OF THE INVENTION

This invention relates to a method of inspecting a resist layer on a gravure printing plate, and a device for practicing the method.

In general, the material of a gravure printing plate is copper. Recesses different in depth according to the light and shade of a picture to be printed are formed in a copper plate to provide a printing plate. The recesses are formed by etching the copper plate with an etching liquid essentially containing ferric chloride. In this etching operation, a gelatin resist layer (carbon tissue) is used as resist in etching. The gelatin resist layer is partially different in thickness according to the light and shade of a picture to be printed before the gravure printing plate is subjected to the etching, so that the etching liquid reaches the copper plate in different times depending on the different thickness. That is, as the total time required for etching the copper plate is controlled by the presence of the gelatin resist layer, the recesses different in depth according to the light and shade of the picture are formed in the copper plate, whereby the aimed printing plate is provided.

The time required for the etching liquid to permeate the gelatin resist layer depends not only on the thickness of the gelatin resist layer but also other various factors such as the density of the etching liquid, the temperature of the etching liquid, and the amount of water contained in the gelatin. Accordingly, the processes of manufacturing gravure printing plates are strictly controlled. However, the characteristics of a gelatin resist layer are liable to be varied by unexpected factors. Therefore, the fluctuations characteristic of the gelatin resist layer are, in general, corrected by adjusting the etching conditions while etching is being carried out. This method may be effective in the case where the degree of fluctuation in characteristic of the gelatin resist layer is small. However, if the degree of fluctuation is large, then it is impossible for the method to adjust the etching conditions suitably, as a result of which the depths of the recesses formed by etching the copper plate become out of the allowable depth range, and the resultant printing plate cannot be used. In addition, the method is disadvantageous in that it takes a relatively long period of time to manufacture a gravure printing plate in addition to the waste of the material (or the printing cylinder).

In order to overcome this difficulty, a visual inspecting method has been employed, in which the degree of advancement of etching is visually inspected with a tone scale or by referring to a picture to be formed.

When the etching liquid essentially consisting of ferric chloride ($FeCl_3$) permeates the gelatin resist layer to reach the surface of the copper plate of the printing plate, the copper (Cu) reacts with the etching liquid to produce cupric chloride ($CuCl_2$), and the ferric chloride ($FeCl_3$) becomes ferrous chloride ($FeCl_2$).

$$FeCl_3 + 3H_2O \rightleftarrows Fe(OH)_3 + 3HCl$$
$$Cu + FeCl_3 \rightarrow CuCl + FeCl_2$$
$$CuCl + FeCl_3 \rightarrow CuCl_2 + FeCl_2$$
$$\overline{Cu + 2FeCl_3 \rightarrow CuCl_2 + 2FeCl_2}$$

In general, the gelatin resist contains a red pigment, and therefore its color is similar to that of the surface of the copper plate. However, as the copper plate is etched, the color of the gelatin resist layer looks black. Therefore, by observing this change, permeation of the etching liquid can be confirmed. On the other hand, the characteristic of the gelatin resist layer can be inspected by comparing the time interval which elapses from the time instant that the etching liquid is dropped until etching is started with a reference time. This inspection method can be achieved readily by dropping the etching liquid onto a region of the gelatin resist layer, which does not directly relate to printing. However, the inspection method is still disadvantageous in the following points:

(1) The time required for the inspection is substantially equal to that required for actually carrying out the etching.

(2) If an etching liquid low in density and high in permeation speed is employed as the inspecting etching liquid, and mutual relation between the inspecting etching liquid and the etching operation is suitably established, then the inspection time may be reduced. However, even if the etching liquid reaches the surface of the copper plate, the gelatin resist layer does not change its color abruptly. In addition to this, the arrival of the etching liquid to the surface of the copper plate is detected visually. Thus, errors in detection are similarly caused.

(3) In this inspection, the inspection region is etched. Therefore, the inspection region must be selected at a position on the printing plate, which does not directly concern printing; however, it is often difficult to select such a position.

(4) If, as a result of the inspection, the resist layer is found so unsatisfactory that it cannot be corrected in the following process, then the resist layer should be removed from the printing plate so that the latter can be used again. However, the inspection region, being etched, will become an obstruction against the re-use of the printing plate.

As the inspection carried out before the etching process has no particular merits as described above, in the existing circumferences the above-described etching operation is carried out while the characteristic of the resist layer is being inspected. In other words, while the degree of advancement of etching is being visually determined with a tone scale or by referring to a picture to be printed, etching liquids different in permeation speed are selectively used according to whether the etching speed is higher than or lower than a reference value, so that the etching operation is achieved within the predetermined allowance. However, in such a method, the characteristic of the resist layer is inspected indirectly in the course of etching control. Therefore, the method is disadvantageous in that, even if any etching control method is employed, the etching is advanced over its control range, as a result of which the printing plate is finished unsatisfactorily.

SUMMARY OF THE INVENTION

Accordingly, an object of this invention is to provide a method in which the conditions of a resist layer on a gravure printing plate can be readily and positively inspected before an etching process is carried out, and a device for practicing the method.

Another object of the invention resides in that etching conditions are made most suitable according to the results of inspection of a resist layer on a gravure printing plate, thereby improving the quality of the gravure printing plate while simplifying the printing plate correcting work in the following process.

A further object of the invention is to provide a method in which a resist layer on a gravure printing plate can be inspected with high accuracy, objectively and without personal errors, and an inspecting device can be readily and stably mounted on the resist layer on the gravure printing plate.

The nature, principle and utility of the invention will become more apparent from the following detailed description when read in conjunction with the accompanying drawings.

BRIEF DESCRIPTION OF THE DRAWINGS

In the accompanying drawings:

FIG. 1 is an explanatory diagram showing the arrangement of a detecting probe employed in this invention;

FIG. 2 is an explanatory diagram showing a state of the detecting probe in operation;

FIG. 3 is a block diagram showing one example of a time measuring circuit according to one embodiment of the invention;

FIGS. 4 and 5 are diagrams for a description of the operation of the time measuring circuit;

Figure 14:
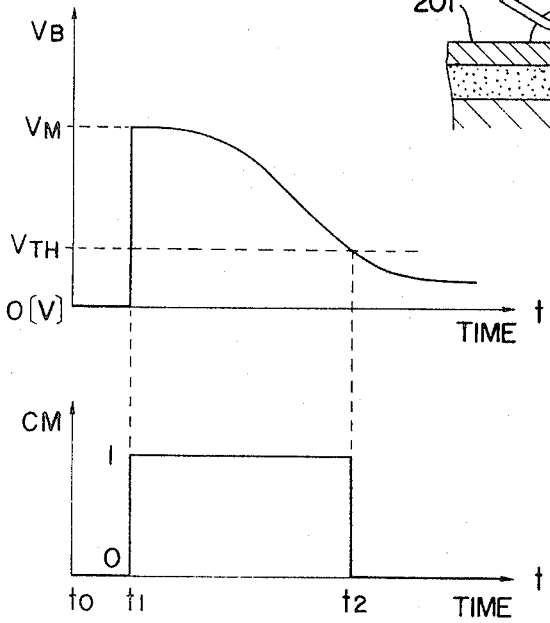
Figure 15:
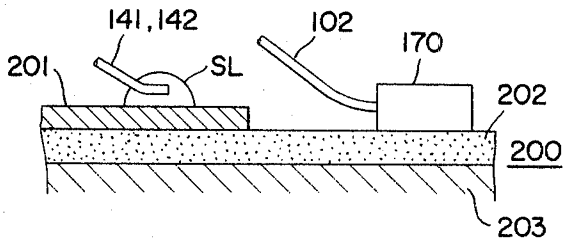
Figure 13:
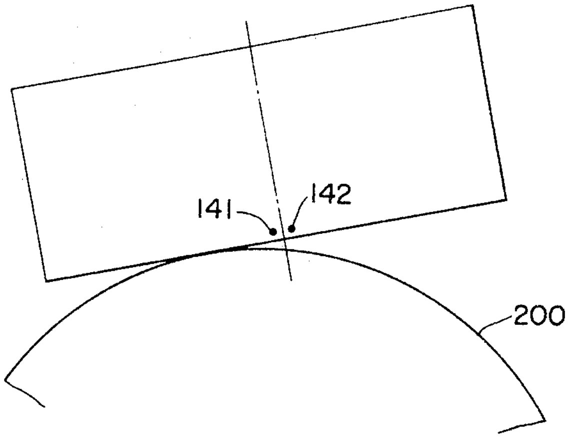
Figure 13:
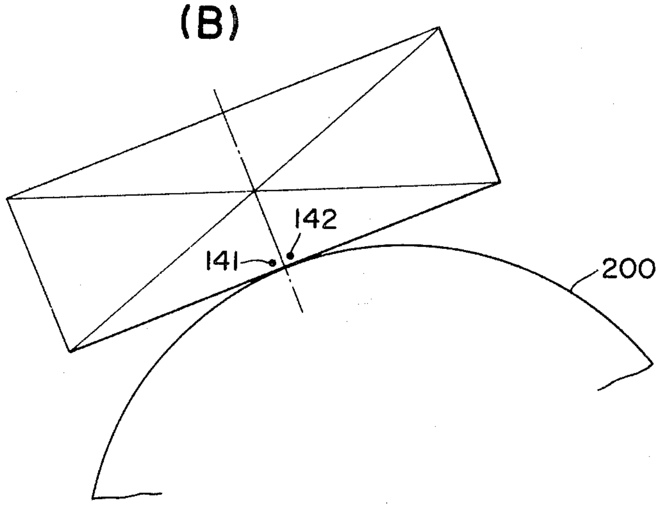

The parts (A) and (B) of FIG. 13 are explanatory diagrams for a description of a method of mounting the inspecting device on a gravure printing plate;

FIG. 14 contains time charts showing one example of the operation of the inspecting device of the invention; and FIG. 15 is an explanatory diagram showing an inspecting liquid dropped onto the resist layer.

DETAILED DESCRIPTION OF THE INVENTION

In this invention, a detecting probe 10 is employed which, as shown in FIG. 1, comprises: a resistor R which is incorporated in the probe 10 and is connected in parallel to the resistance of a resist layer; a pair of conductors or detecting pieces 1 and 2; and output terminals A, B and C.

As shown in FIG. 2, the output terminal C of the probe 10 is brought into contact with a printing plate (copper) 11, and the detecting pieces 1 and 2 are placed over a desired region of a resist 12 on the printing plate 11, which is to be inspected. Under this condition, an electrically conductive inspecting liquid 13 is allowed to drop to the inspection region from above the detecting pieces 1 and 2.

On the other hand, the output terminals A and B are connected to a time measuring circuit 20 as shown in FIG. 3. The time measuring circuit 20 is connected through a connecting block 21 to terminals D1 and D2, which are connected respectively to the output terminal of an operational amplifier 22 and to the negative input terminal of the operational amplifier 22. The negative input terminal of the operational amplifier 22 is connected through a sensitivity adjusting variable resistor R1 to a negative voltage source −V, and the positive input terminal is grounded. A feed-back resistor R2 is connected between the output terminal and the negative input terminal of the operational amplifier 22, the resistor R2 being connected in parallel to the resist resistance.

Further referring to FIG. 3, the output AS of the operational amplifier 22 is applied to comparators 23 and 24, where it is compared with reference voltages VS1 and VS2 respectively. The comparison outputs C1 and C2 of the comparators 23 and 24 are applied to an AND circuit AD, the output of which is applied to one input terminal of an NAND circuit ND, to the other input terminal of which the pulse output PS of an oscillator 25 is applied. The output PC of the NAND circuit ND is applied to a counter 26. The count value of the counter 26 is applied through a decoder 27 to a display circuit 28, where it is displayed. The counter 26 is reset by means of a switch SW1. The output pulse PS of the oscillator 25 is a repetitive pulse having a predetermined frequency. The reference voltages VS1 and VS2 applied to the comparators 23 and 24 are preset to predetermined values in advance.

Before the inspection liquid 13 drops onto the detecting pieces 1 and 2 of the detecting probe 10, the terminals A and B are electrically separated from each other, and therefore the resistance between the two inspecting terminals A and B is substantially infinite as indicated at the time instant $t_0$ in FIG. 4. Accordingly, the feedback resistance of the operational amplifier 22 is only the resistance R2, and the output C1 of the comparator 23 is raised to a logical level "1" (hereinafter referred to merely as "1"), while the output C2 of the comparator 24 is set to a logical level "0" (hereinafter referred to merely as "1"). Therefore, the output C3 of the AND circuit AD is set to "0". Accordingly, the output pulse PS of the oscillator 25 is blocked by the NAND circuit ND, and the counter 26 carries out no counting operation.

When the inspecting liquid 13 is dropped onto the detecting pieces 1 and 2 of the detecting probe 10 (time instant $t_1$), the detecting pieces 1 and 2 are electrically coupled to each other since the inspecting liquid 13 is electrically conductive as described above. Therefore, the resistance between the terminals A and B as viewed from the device becomes that of the resistor R from the time instant $t_1$. That is, the resistor R is connected in parallel to the resistor R2. Accordingly, the feedback resistance of the operational amplifier 22 is $(R \cdot R2)/(R+R2)$, and therefore the output C2 of the comparator 24 is raised to "1". In this operation, the output of the comparator 23 is maintained unchanged at "1". Thus, the output C3 of the AND circuit AD is raised to "1" at the time instant $t_1$ as shown in FIG. 5. The pulse output PS of the oscillator 25 is applied through the NAND circuit ND to the counter 26, and therefore the counter 26 starts its counting operation.

The count value of the counter 26 is converted into time data by the decoder 27, so that the lapse of time from the counting operation start time instant is displayed by the display circuit 28.

When the inspecting liquid 13 is dropped onto the resist layer 12, then the inspecting liquid 13 gradually permeates the resist layer 12, and finally reaches the printing plate 11 (time instant $t_2$). As a result, the terminal A is electrically coupled through the printing plate 11 to the terminal C. In other words, the resistance between the terminals A and B becomes low at the time instant $t_2$ as shown in FIG. 4. Accordingly, the feedback resistance of the operational amplifier 22 is also decreased, whereby the output C1 of the comparator 22 is set to "0", while the output C3 of the comparator 23 is raised to "1". Thus, the output C3 of the AND circuit AD is set to "0" at the time instant $t_2$, as shown in FIG. 5. Therefore, at the time instant $t_2$, the output pulse PS of the oscillator 25 is blocked by the NAND circuit ND, and the counting operation of the counter 26 is suspended. Thus, for the period of time from the time instant $t_1$ to the time instant $t_2$, i.e. for the period of time which elapse from the time instant that the inspecting liquid 13 is dropped onto the resist layer 12 until the inspecting liquid 13 permeates the printing plate 11, the counter 26 counts the output pulses PS provided by the oscillator 25. The count value of the counter 26 is converted into time data by the decoder 27, the time data is displayed by the display circuit 28.

Figure 6:
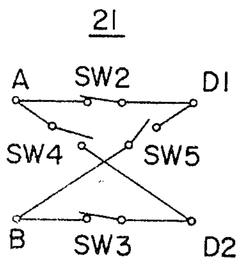
FIG. 6 is a circuit diagram showing a connecting block employed in another embodiment of the invention.
Figure 7:
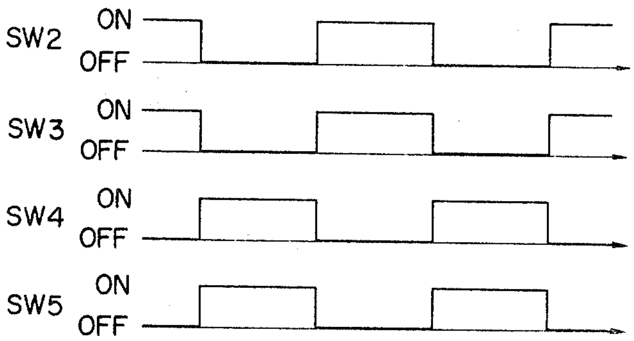
FIG. 7 contains diagrams for a description of the operation of the connecting block in FIG. 6.

In the above-described embodiment of the invention, the inspection is carried out in a DC mode. However, it is possible to carry out the inspection in an AC mode. In the latter case, it is essential that the inspecting liquid is not subjected to electrolysis. For this purpose, the connecting block 21 is modified as shown in FIG. 6. More specifically, switches SW2 through SW5 are connected in the form of bridges between the terminals A and B, and the terminals D1 and D2. These switches SW2 through SW5 are operated on and off as indicated in FIG. 7. When the switches are operated, noise may be caused. In order to obtain smoothed signal components by eliminating the noise, a capacitor is connected in parallel to the resistor R2 of the operational amplifier 22.

In the embodiment shown in FIG. 3, the negative input terminal of the operational amplifier 22 is connected through the variable resistor R1 to the negative voltage source −V. However, the inspection may be carried out in an AC mode by employing an AC pulse source instead of the voltage source −V.

Figure 8:
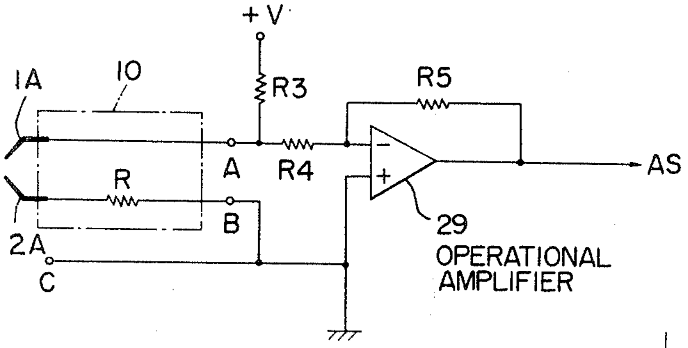
FIG. 8 is a circuit diagram, partly as a block diagram, showing a third embodiment of the invention.
Figure 9:
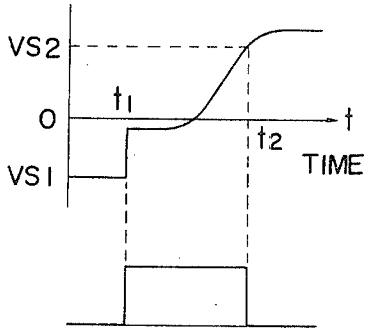
FIG. 9 contains diagrams for a description of the operation of the third embodiment of the invention.

If the detecting pieces of the detecting probe 10 are made of a material, such as platinum, which is different from the material comprising the printing plate 11, which may be copper, and the inspecting liquid is electrolytic, then when the inspecting liquid reaches the printing plate 11, the detecting pieces are electrically coupled to the printing plate 11, as a result of which a potential is generated between the copper of the printing plate 11 and the platinum of the detecting pieces. Therefore, the time can be measured by detecting the potential. In this case, the detecting circuit is provided by combining resistors R3 through R5 and an operational amplifier 29 as shown in FIG. 8, and the output AS is as indicated in the upper part of FIG. 9. Threshold values are set as indicated by the reference voltages VS1 and VS2 in the upper part of FIG. 9, then the measurement can be carried out similarly as in the above-described embodiment.

Figure 10:
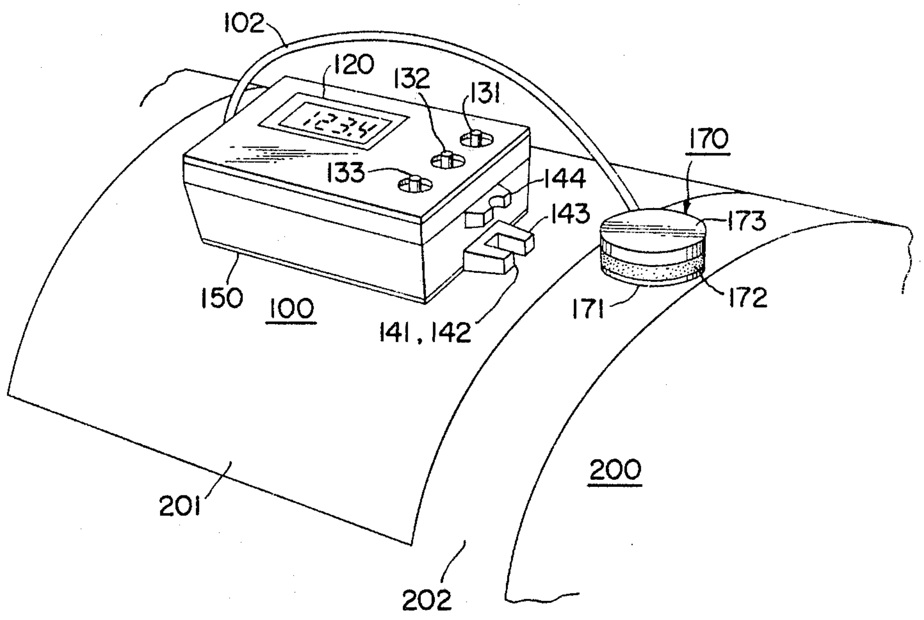
FIG. 10 is a perspective view showing the external appearance and use of one example of an inspecting device according to the invention.
Figure 11:
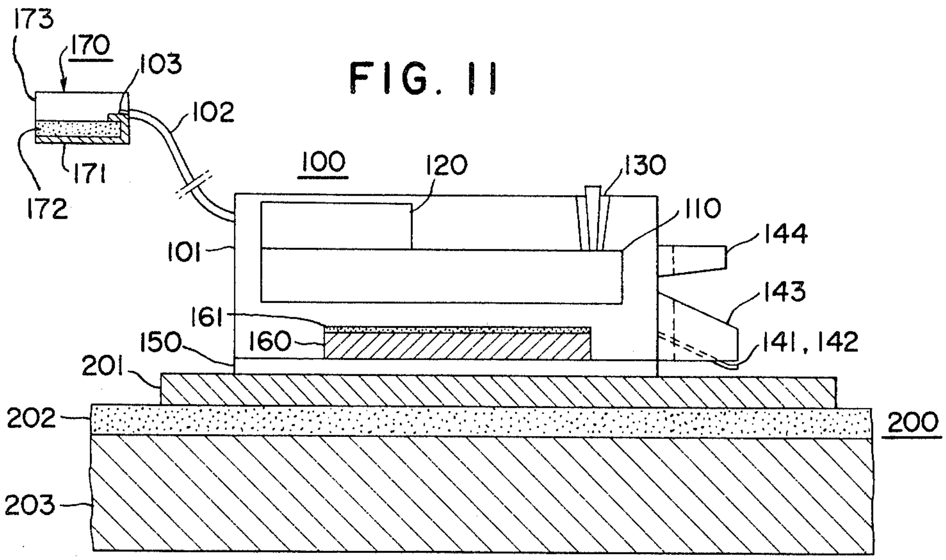
FIG. 11 is a sectional view showing the inspecting device in FIG. 10 and a gravure printing plate on which the inspecting device is mounted.

FIGS. 10 and 11 show the concrete arrangement of another embodiment of the invention.

An inspecting device 100 is placed on a resist layer 201 formed on a cylindrical gravure printing plate 200 which is constituted by the outer layer or copper plate 202 and the inner layer or iron plate 203.

The inspecting device 100 comprises: a casing 101 incorporating a measuring circuit 110 (described later), a display section 120 and an operating section 130; electrodes 141 and 142 which are provided on one side wall of the casing 101 so that they are brought in contact with an inspection region of the resist layer 201 through an inspecting liquid (hereinafter referred to as "resist electrodes 141 and 142" when applicable); a rubber sheet 150 provided on the bottom of the casing 101; a magnet 160 with an iron plate 161 provided on the rubber sheet 150; and a cylinder electrode 170 connected through a lead wire 102 to the casing 101.

The resist electrodes 141 and 142 are surrounded by a U-shaped electrode guide 143, and a U-shaped filler retaining member 144 for stably retaining an inspecting liquid dropping filler is provided above the electrode guide 143.

The operating section 130 is provided with a power "on" button 131, a power "off" button 132, and a clear button 133. The resist electrodes 141 and 142 are connected through lead wires to the measuring circuit 110, and the cylinder electrode 170 is connected through the lead wire 102 to the measuring circuit 110.

The bottom of the cylinder electrode 170 is covered with a copper plate 171, and a magnet 172 is provided on the copper plate 171 to cause the cylinder electrode 170 to be fixedly retained on the iron plate 102 of the cylinder. The upper surface of the magnet 172 is covered with a resin layer 173. The copper plate 171 on the bottom of the cylinder electrode 170 is connected through a conductor 103 in the lead wire 102 to the measuring circuit.

Figure 12:
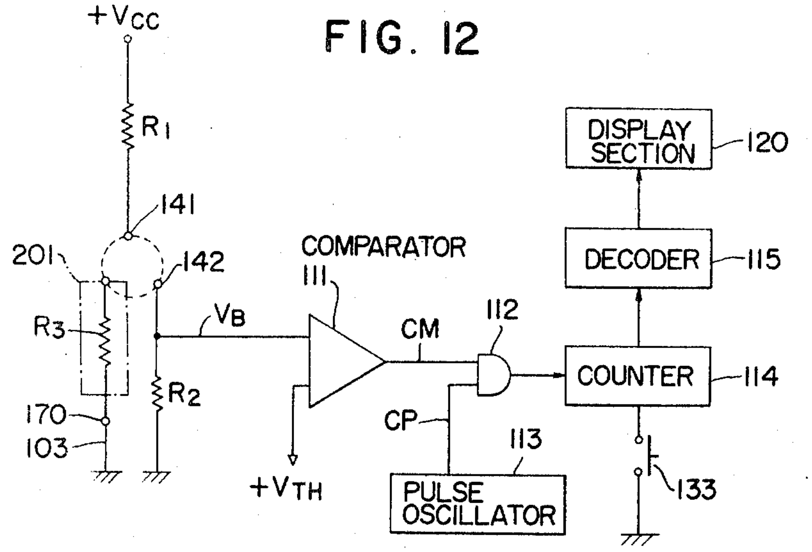
FIG. 12 is a circuit diagram, partly as a block diagram, showing one example of a measuring circuit in the inspecting device according to the invention.

Connection of the electrodes 141, 142 and 170 to the measuring circuit 110 and the arrangement of the latter 110 are as shown in FIG. 12. More specifically, the resist electrode 141 is connected through a resistor R1 to an electric source +Vcc, while the resist electrode 142 is grounded through a resistor R2. A potential $V_B$ developed at the resist electrode 142 is applied to a comparator 111 which is set to a threshold potential $V_{TH}$. The output CM (binary signal) of the comparator 111 is applied to one input terminal of an AND circuit 112, to the other input terminal of which is applied a clock pulse CP having a predetermined frequency from a pulse oscillator 113. The output of the AND circuit 112 is counted by a counter 114. The count value of the counter 114 is converted into a permeation time data by a decoder 115, which is displayed by the display section 120. The count value of the counter 114 is cleared by operating the clear button 113. In FIG. 12, reference character R3 designates the resistance of the resist layer 201 being measured.

The inspecting device is placed on the resist layer 201. When the inspection device is set, with the aid of the gravity and frictional force, on an object such as a cylinder which is curved and sloped, then the resist electrodes 141 and 142 are unequally spaced apart from the resist layer 201 formed on the printing plate 200 as shown in the part (A) of FIG. 13. This difficulty has been eliminated according to the invention. That is, in the invention, the magnet 160 is uniformly arranged on the bottom of the inspecting device, so that the inspecting device is set in contact with the resist layer at the central portion by the attraction force caused between the magnet 160 and the iron plate 203 in the printing plate 200 at all times, as shown in the part (B) of FIG. 13. Thus, the resist electrodes 141 and 142, being provided at the central portion of the inspecting device, are maintained equally spaced apart from the measuring surface of the resist layer, as a result of which the measurement can be stably carried out at all times. The iron plate 161 on the magnet 160 is to increase the attraction force of the magnet 160, and the rubber sheet 150 is to protect the surface of the resist layer 201.

The inspecting device is mounted on the printing plate 200 as described above so that the resist electrodes 141 and 142 are set above a desired region of the resist layer 201, while the cylinder electrode 170 is mounted on the copper plate 202 of the printing plate 200. In this case, since the magnet 172 is provided on the bottom of the cylinder electrode 170, the cylinder electrode 170 is stably and fixedly mounted on the copper plate 202 by the attraction force which is caused between the magnet 172 and the iron plate 203 of the printing plate 200 as shown in FIG. 10.

The inspection is started upon depression of the power "on" switch 131. Since, in this operation, the resist electrode 142 is grounded through the resistor R2, its potential $V_B$ is at O V for the period of time from the time instant $t_0$ to the time instant $t_1$ the upper part in FIG. 14, and is lower than the threshold potential $+V_{TH}$. Accordingly, the output of the comparator 111 is at "0" (cf. the lower part of FIG. 14). Therefore, the clock pulse CP is blocked by the AND circuit 112, and the counter 114 carries out no counting operation.

Under this condition, an electrically conductive inspecting liquid SL is dropped onto the resist electrodes 141 and 142 with the filler. More specifically, the body of the filler is abutted against the filler retaining member 144 to allow the inspecting liquid SL to drop onto the resist electrodes 141 and 142 as shown in FIG. 15. The electrically conductive inspecting liquid SL is brought into contact with the resist layer 201 and the resist electrodes 141 and 142. Accordingly, when the inspecting liquid is dropped as described above, i.e. at the time instant $t_1$ (FIG. 14), current from the electric source +Vcc flows in the resistors R2 and R3 through the resistor R1. As a result, the potential $V_B$ is raised to the voltage division value $V_M$ of the resistance R1 and the composite resistance of the resistances R2 and R3 (cf. the part (A) of FIG. 14). The voltage division value $V_M$ is applied to the comparator 111. As the value $V_M$ is higher than the threshold potential $+V_{TH}$, the output CM of the comparator 111 is raised to "1" (cf. the lower part of FIG. 14). Hence, the clock pulse CP is applied through the AND circuit 112 to the counter 114, and the counting operation is started by the counter 114. The count value of the counter 114 is converted into a time data by the decoder 115, and the lapse of time from the count start time instant $t_1$.

After being dropped onto the resist layer 201, the inspecting liquid SL gradually permeates the resist layer 201, and therefore the resistance of the resist layer 201 is gradually decreased. That is, from the time instant $t_1$ the potential $V_B$ is gradually decreased and finally becomes lower than the threshold potential $V_{TH}$ (at the time instant $t_2$) as shown in the upper part of FIG. 14. As a result, the output CM of the comparator 111 is set to "0" again, the clock pulse CP from the pulse oscillator 113 is blocked by the AND circuit 113, and the counting operation of the counter 114 is suspended. Thus, for the period of time from the time instant $t_1$ to the time instant $t_2$, i.e. for the time interval which elapses from the time instant that the inspecting liquid is dropped until the inspecting liquid permeates the resist layer to a predetermined depth (corresponding to the threshold potential $V_{TH}$), the counter 114 counts the clock pulses CP from the pulse oscillator 113. The count value of the counter 114 is converted into a time data by the decoder 115, and the time data is displayed, as a permeation time, by the display device 120. Thus, the permeation time of the inspecting liquid in the resist layer 201 has been measured. The count value of the counter 114 can be reset by operating the clear button 133.

As is apparent from the above description, the inspecting method and apparatus according to the invention make it possible to inspect the conditions of a resist layer before the etching process is carried out. In the case when the resist layer of a printing plate is found unsatisfactory as a result of the inspection, the expensive printing plate can be used merely by forming the resist layer again. Furthermore, most suitable etching conditions can be determined from the inspection result, which contributes to an improvement of the quality of the printing plate, and to relieving the burden of printing plate correction in the following process.

In addition, it can be determined from the inspection result whether or not the preceding process is acceptable; that is, the inspection result can be utilized as control data for all the processes of manufacturing printing plates.

Any liquid can be used as the inspecting liquid, if it is electrically conductive. If a non-corrosive liquid is used, then the printing plate can be inspected without forming traces thereon. With the printing plate, the resultant prints are clear.

The inspecting method and apparatus of the invention can select any inspection region on a gravure printing plate, which contributes to an improvement of the inspection accuracy. The inspecting method of the invention, unlike the visual inspecting method using human eyes, employs the electrical circuit, and therefore its inspection results are objective; that is, the inspection is carried out accurately without personal errors.

The inspecting device can be readily and stably mounted on the resist layer on a gravure printing plate and the measurement can be carried out even by an unskilled person.

What is claimed is:

1. A method of inspecting a resist layer on a gravure printing plate, comprising:

dropping an electrically conductive inspecting liquid onto a region of the resist layer on the gravure printing plate to be inspected, a pair of detecting pieces being immersed in said liquid dropped on the resist layer, said detecting pieces and the liquid forming an electrically conductive circuit;

bringing a third detecting piece into contact with a material of the gravure printing plate to form an electrical circuit;

allowing the liquid to permeate the resist layer to form a short circuit between the liquid and the material; and inspecting the resist layer by utilizing a period of time required for forming the short circuit.

2. A method as recited in claim 1, further comprising:

connecting a comparison circuit between the electrically conductive circuit and the electrical circuit to detect the formation of the short circuit between the liquid and the material.

3. A method of inspecting a resist layer on a gravure printing plate, comprising:

dropping an electrically conductive inspecting liquid having a pair of detecting pieces immersed therein onto a region of the resist layer on the gravure printing plate to be inspected;

allowing the liquid to permeate the resistlayer to form a short circuit between the liquid and a material of the gravure printing plate; and inspecting the resist layer by utilizing a period of time required for forming the short circuit.

* * * * *